(12) United States Patent
Slazas et al.

(10) Patent No.: US 8,021,352 B2
(45) Date of Patent: Sep. 20, 2011

(54) UNFUSED CATHETER BODY FEATURE AND METHODS OF MANUFACTURE

(75) Inventors: Robert R. Slazas, Miami, FL (US); Jessica T. Schenck, Waltham, MA (US)

(73) Assignee: Codman & Shurtleff, Inc., Raynham, MA (US)

(*) Notice: Subject to any disclaimer, the term of this patent is extended or adjusted under 35 U.S.C. 154(b) by 191 days.

(21) Appl. No.: 11/466,632

(22) Filed: Aug. 23, 2006

(65) Prior Publication Data

US 2008/0051761 A1    Feb. 28, 2008

(51) Int. Cl.
  *A61M 25/00* (2006.01)
  *A61M 31/00* (2006.01)
  *A61M 37/00* (2006.01)
  *A61M 29/00* (2006.01)

(52) U.S. Cl. .......... 604/527; 604/103.09; 604/523; 604/524; 604/525; 604/526; 604/915; 604/96.01

(58) Field of Classification Search .......... 604/103.09, 604/523, 524, 526, 527, 93.01, 96.01, 915, 604/264, 48, 525
See application file for complete search history.

(56) References Cited

U.S. PATENT DOCUMENTS

| | | | | |
|---|---|---|---|---|
| 4,009,734 A * | 3/1977 | Sullivan | ................. | 138/125 |
| 4,572,186 A * | 2/1986 | Gould et al. | ................. | 606/194 |
| 4,597,755 A * | 7/1986 | Samson et al. | .......... | 604/103.09 |
| 5,496,275 A | 3/1996 | Sirhan et al. | | |
| 5,522,818 A * | 6/1996 | Keith et al. | ............ | 604/103.09 |
| 5,538,513 A * | 7/1996 | Okajima | ................. | 604/527 |
| 5,755,704 A * | 5/1998 | Lunn | ................. | 604/527 |
| 5,911,715 A * | 6/1999 | Berg et al. | ................. | 604/525 |
| 5,997,487 A * | 12/1999 | Kolehmainen et al. | ....... | 600/585 |
| 6,273,879 B1 * | 8/2001 | Keith et al. | ................. | 604/523 |
| 6,315,757 B1 * | 11/2001 | Chee et al. | ............ | 604/103.09 |
| 6,344,029 B1 * | 2/2002 | Estrada et al. | ........... | 604/103.09 |
| 6,511,471 B2 | 1/2003 | Rosenman et al. | | |
| 6,629,952 B1 * | 10/2003 | Chien et al. | ............ | 604/103.09 |
| 6,706,010 B1 | 3/2004 | Miki et al. | | |
| 6,893,456 B2 | 5/2005 | Lumauig | | |
| 7,001,369 B2 | 2/2006 | Griffin et al. | | |
| 7,195,611 B1 * | 3/2007 | Simpson et al. | ......... | 604/103.04 |
| 2004/0186506 A1 | 9/2004 | Simpson et al. | | |
| 2005/0010194 A1 * | 1/2005 | Zhou | ................. | 604/527 |

(Continued)

FOREIGN PATENT DOCUMENTS

EP    0555088 A2    8/1993

(Continued)

OTHER PUBLICATIONS

Shore (Durometer) Hardness Testing of Plastics, MatWeb Material Property Data, http://www.matweb.com/reference/shore-hardness.aspx.*
European Search Report for European patent application No. 07252846.6, dated Nov. 8, 2007.

*Primary Examiner* — Theodore Stigell
*Assistant Examiner* — Shefali Patel
(74) *Attorney, Agent, or Firm* — Cook Alex Ltd.

(57) ABSTRACT

The disclosure is directed to tubular bodies for catheters. An inner tubular catheter body has an inner layer, a braided portion over the inner layer and an outer layer. The outer layer is fused to the braided portion for a selected length or lengths of the inner tubular body and is unfused for a selected length or lengths to achieve the desired combination of stiffness and flexibility.

19 Claims, 2 Drawing Sheets

U.S. PATENT DOCUMENTS

| | | |
|---|---|---|
| 2005/0154414 A1 | 7/2005 | Perreault et al. |
| 2005/0288628 A1 | 12/2005 | Jordan et al. |
| 2006/0030835 A1 | 2/2006 | Sherman et al. |
| 2006/0129176 A1 | 6/2006 | Griffin et al. |
| 2007/0083188 A1* | 4/2007 | Grandt et al. ............... 604/524 |
| 2007/0250040 A1* | 10/2007 | Provost et al. ............... 604/525 |

FOREIGN PATENT DOCUMENTS

| | | |
|---|---|---|
| EP | 0778037 A1 | 6/1997 |
| EP | 1121955 A2 | 8/2001 |
| WO | WO 99/17827 A | 4/1999 |

* cited by examiner

UNFUSED CATHETER BODY FEATURE AND METHODS OF MANUFACTURE

FIELD OF THE INVENTION

The disclosure relates to tubular bodies of catheters designed to deliver devices that are used to treat or diagnose defects in the vasculature. The tubular bodies of the catheters are enhanced in flexibility and bendability while exhibiting good column strength. Special application is found for inner catheter bodies, most particularly at distal locations of an inner catheter body.

BACKGROUND OF THE INVENTION

The intraluminal delivery of diagnostic catheters, treatment fluids, expansion devices or stents is commonly used to diagnose or treat defects, such as blockages and stenoses, within the human vasculature. Expansion devices can take a number of forms, including a balloon that is inflated to open the blockage. The use of a balloon may provide only a temporary solution and a stent may be inserted after or instead of the balloon as a more permanent solution.

When treating defects in peripheral, coronary or neural blood vessels, it is usually necessary to pass the treatment or diagnostic device through tortuous paths in the vasculature, and often through narrow constrictions, to reach the desired site. To accomplish this, the devices often are delivered by a catheter. Catheters generally have a tubular shaft with a lumen and may include an inner member. To guide the catheter through the vasculature to the desired site, catheters can be passed over a guidewire.

The parameters of trackability, pushability and crossability are often assessed when discussing catheter performance. An optimal design would allow the catheter to easily follow the path of the vasculature (trackability) and to readily traverse narrow constrictions in the vasculature (crossability) but would not substantially affect the ability to transmit force from the proximal end to the distal end of the catheter (pushability).

Trackability and crossability are improved by the properties of the most distal portion of the catheter: A flexible distal portion improves performance of the catheter with respect to these parameters. However, the catheter body must not be too flexible or pushability will be adversely affected. To attempt to reconcile these differing requirements, catheters have been designed that have a flexible distal portion but a stiffer proximal portion. However, these catheters often require elaborate designs that are difficult to manufacture. For example, Griffin et al., U.S. Pat. No. 7,001,369 describes a device that requires multiple reinforcement layers and the use of several types of materials to achieve the required properties. Other devices having catheter shaft variations are found in Jordan et al. U.S. Patent Application Publication No. 2005/0288628 and Sherman et al. U.S. Patent Application Publication No. 2006/0030835. Each patent or publication referred to is herein incorporated by reference.

A need remains for an effective but simple-to-use and easily manufactured catheter structure that allows for flexibility while maintaining adequate stiffness in important areas of the inner tubular body of the catheter. At times it is desired to have a catheter inner tubular body that allows for flexibility or stiffness in selected areas.

SUMMARY

In one embodiment, the disclosure is directed to catheters with inner tubular bodies where the inner tubular body has an inner layer, a braided portion extending over at least part of the inner layer and an outer layer that extends over the braided portion. The outer layer is fused to the braided portion for one or more selected lengths and is unfused to the braided portion for one or more other lengths.

In another embodiment, the disclosure is directed to catheters with inner tubular bodies where the inner tubular body has an inner layer, a braided portion extending over at least part of the inner layer and an outer layer that extends over the braided portion. The outer layer is fused to the braided portion for one or more selected lengths and is unfused to the braided portion for one or more other lengths, and the outer layer has the same composition over its entire length.

In another embodiment, the disclosure is directed to balloon catheters with inner tubular bodies where the inner tubular body has an inner layer, a braided portion extending over at least part of the inner layer and an outer layer that extends over the braided portion. The outer layer is fused to the braided portion for a length of the distal portion of the catheter and is unfused to the braided portion for over at least part of the length that the balloon overlies.

The disclosure is also directed to methods of manufacture of inner tubular bodies where an inner layer is applied to the surface of a mandrel, a braided portion is applied to the outside surface of said inner layer, an outer layer is applied around the braided portion and the inner layer and then one or more selected lengths of the outer layer is or are fused to the braided portion. One or more lengths remain unfused. The mandrel is removed to form a inner tubular member.

DESCRIPTION OF THE PREFERRED EMBODIMENTS

As required, detailed embodiments of the present disclosure are presented herein; however, it is to be understood that the disclosed embodiments are merely exemplary, which may be embodied in various forms. Therefore, specific details disclosed herein are not to be interpreted as limiting, but merely as a basis for the claims and as a representative basis for teaching one skilled in the art to variously employ the embodiments of the disclosure in virtually any appropriate manner.

The disclosure relates to inner tubular bodies for catheters. In general, the inner tubular bodies have an inner layer that defines a lumen, a braided portion that extends over at least a portion of the inner layer and an outer layer that extends over the braided portion. The outer layer is fused to the braided portion for one or more selected lengths and is unfused for one or more selected lengths. The inner tubular bodies of the present disclosure may be used for catheters designed for peripheral, coronary or neurovascular applications.

Figure 1:
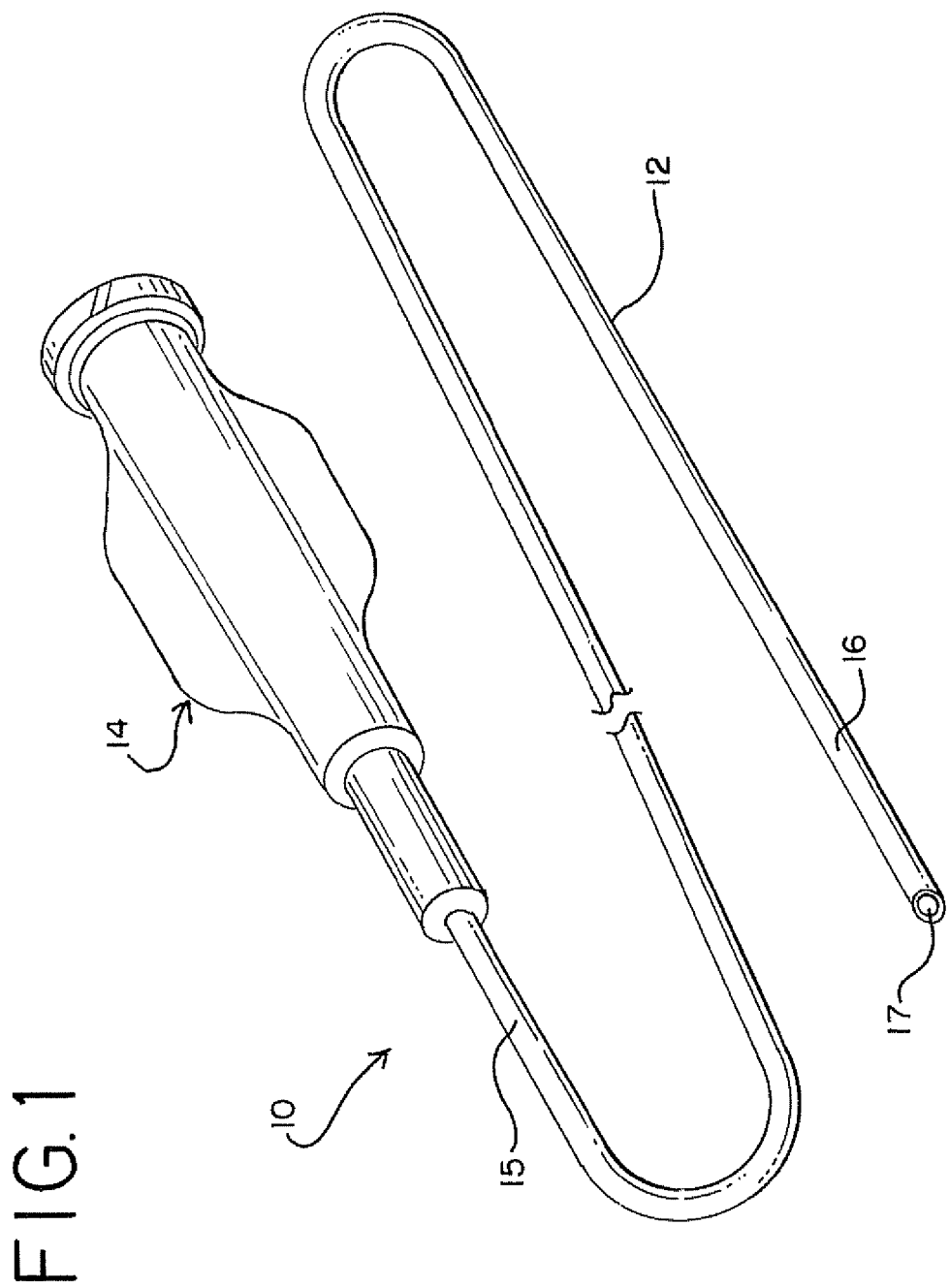
FIG. 1 is a perspective view of a medical device catheter.

FIG. 1 shows one embodiment of a catheter according to the disclosure. The catheter 10 has a long flexible tubular shaft 12 that extends from a proximal portion 15 to a distal end portion 16. A hub 14 is present at the proximal end of the shaft. Catheter 10 defines at least one passage or lumen 17.

Figure 2:
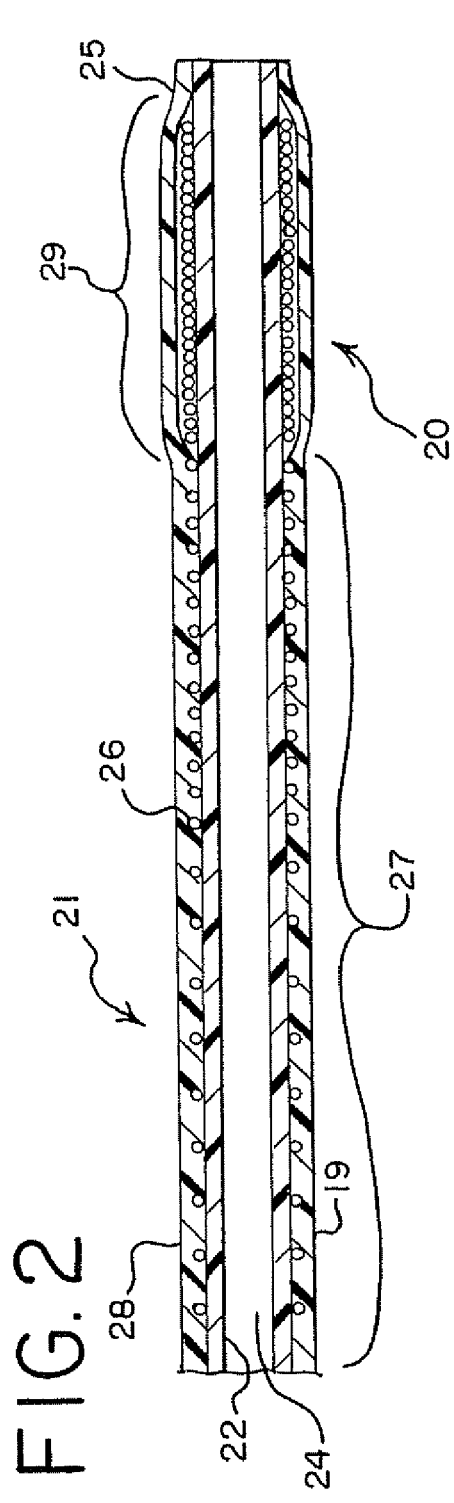
FIG. 2 is a longitudinal cross-sectional view of a catheter including a braided tube assembly.

FIG. 2 shows one embodiment of a cross-sectional view of a tubular body according to the disclosure. The tubular body 21, with proximal portion 19 and distal end portion assembly 20, generally has an inner layer 22 that defines a lumen 24, a braided portion 26 that extends over the inner layer, and an outer layer 28 that extends over the braided portion 26. According to the present disclosure, the outer layer 28 is fused to the braided portion 26 for a selected length 27 and is unfused for a selected length 29. The most distal portion 25 of the outer layer may also fused to the braided portion. Also, the outer layer typically will be fused to the inner layer at the fused length.

In a preferred embodiment, a selected length of the proximal portion of the outer layer is fused to the braided portion while a length of distal portion is unfused. In this and similar embodiments, the unfused distal portion has greater flexibility, allowing it to bend more easily and thereby facilitating its movement through the vasculature. For example, the braided portion components are more able to slide with respect to each other in the unfused portion. The fused proximal portion is stiffer and thereby facilitates the pushing of the catheter through the vasculature. In the fused portion, the braided portion components become relatively fixed due to fusion to the outer layer, resulting in a stiffer proximal portion.

Figure 3:
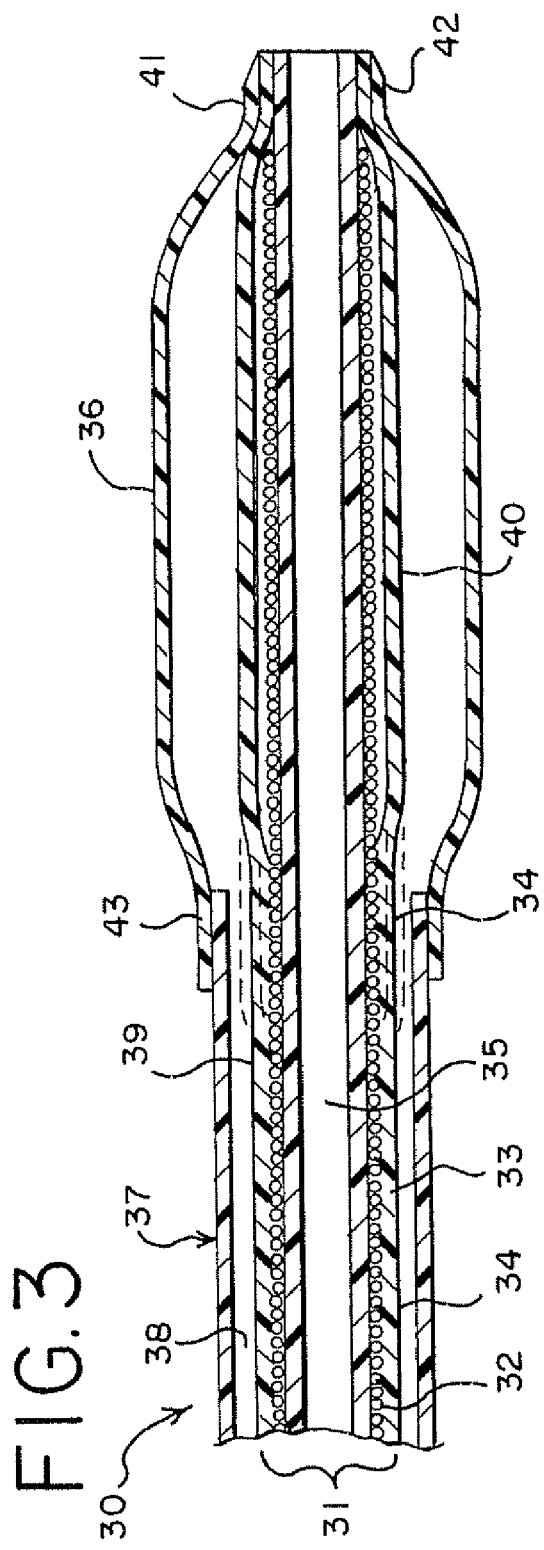
FIG. 3 is a longitudinal cross-sectional view of a distal portion of catheter having a tubular inner body and a balloon component.

FIG. 3 shows a cross-sectional view of one embodiment of a balloon catheter 30 according to the present disclosure. An inner tubular body 31 has a inner layer 32, a braided portion 33 and an outer layer 34 and defines a lumen 35. A balloon 36 is attached to the inner tubular body at its distal end along balloon distal leg 42, and the balloon is attached to an outer tubular body 37 at its proximal end along balloon proximal leg 43. The balloon may be composed of a variety of materials including those known in the art such as nylon, PEBAX or silicone urethanes. A second lumen 38 is defined by the annular space between the inner 31 and outer 37 tubular bodies.

In this embodiment, the fused length or region 39 of the outer layer 34 extends from the proximal portion of the catheter to the proximal end of the balloon. What is meant by the proximal end of the balloon can range from radially internal of the proximal end of the proximal leg 43 to the distal end of the proximal leg 43. For example, FIG. 3 shows (in solid lines) the fused length or region 39 extending distally to radially internal of the distal end of the proximal leg 43. Broken lines at this general location illustrate the unfused length extending proximally to radially internal near or beyond the proximal end of the proximal leg 43. In these illustrated embodiments, the unfused length or region 40 begins immediately distal of the distal end of the fused length or region 39.

It is contemplated that the illustrated transitions between these fused and unfused regions also can be positioned between or beyond these explicitly illustrated (in solid or broken lines) locations in this embodiment. Thus, in this embodiment, the unfused length or region 40 extends distally from proximally beyond, at or near the proximal end of the balloon to at or near the distal end of the balloon.

Each unfused portion or region allows for greater flexibility in this area of the balloon and helps compensate for reduced flexibility that may occur due to the presence of the balloon at this location, including when the balloon is deflated and covers the tubular member. The most distal portion of the outer layer may be fused to the braided portion such that the outer layer is held to the braid in this section by means of what may be referred to as ring fuse 41. It is convenient for such a ring fuse or the like to include the distal leg 42 of the balloon.

In a preferred embodiment, the outer layer 28, 34 may have the same composition over its entire length. Preferably, the material or materials selected for the outer layer have a Shore Durometer hardness value equal to or less than about 72D. The material may have a Shore hardness value as soft as about 80A. The Shore hardness can range from about 25D to about 72D. Suitable materials for the outer layer include but are not limited to polyamides, polyimides, nylons, polyethylenes, polyvinylidene fluoride (PVDF), polyesterether block amides, polyurethanes and combinations of these materials. Polyesterether block amides, sold under the Trademark PEBAX by Arkema Inc, are an especially preferred material. Another range of Shore hardness values for PEBAX is from about 35D to about 55D.

The braided portion of the tubular body may be formed from a range of materials. Optimally, the structure of the braided portion should not be compromised when the outer layer is fused to the braided portion. The braided portion may be made of wire made from metals such as platinum or stainless steel. The braided portion may also be made from fibers or filaments made from thermoplastic or thermoset materials. Examples of these include but are not limited to polyamides and liquid crystal polymers such as those sold under the trade name Vectra. The pic values for the braided portion are the range of from about 25 to about 140 pics/inch and preferably from about 60 to 120 pics/inch. A higher pic value affords greater flexibility to the tubular member. In one embodiment, the pic values may be constant over the length of the braided portion. In other embodiments, pic values may vary and consequently the flexibility of the braided portion may vary over the length of the braided portion.

The length, location and number of fused and unfused regions of the outer layer may be adjusted depending on the application. For example, an unfused region may be included in a region where it is necessary to have a braid with a low pic count because of a need to resist torsional strain or some other mechanical requirement. Thus, the inclusion of one or more unfused outer layer portions will increase flexibility in these regions.

An inner tubular member according to the disclosure may be made according to the following method. A core wire or mandrel serves as a foundation, around which the catheter shaft tube is built up. After the tube is fully formed, the mandrel is removed, leaving the inner catheter tubular member. The size of the core wire used for the mandrel will determine the size of the catheter shaft tube lumen, when the core wire is eventually removed. Various materials may be used for the mandrel, including stainless steel or copper, which may be silver-coated. By way of example only, the diameter of the wire/mandrel used to form the lumen for catheters used in neurovascular applications may be from about 0.010 inch to about 0.020 inch.

An inner layer is applied to the core wire by any of several methods: wire mandrel extrusion, dipping or spraying using solvents and/or heat to create a solution of the polymer material, fuse-down techniques such as those employing shrink tubing, or other deposition techniques. According to some embodiments of the present disclosure, the purpose of the inner polymer layer is to provide a lubricious inner surface for the lumen of the resulting tube, rather than to substantially contribute to the catheter shaft performance and structural properties. Accordingly, the inner polymer layer may be very thin, in the range of from about 0.0005 inch to about 0.002 inch. The inner layer may be formed from materials including but not limited to polytetrafluoroethylene (PTFE) expanded polytetrafluoroethylene (EPTFE) or high density polyethylene (HDPE).

The braided portion is added to the outside of the inner polymer layer. By way of example only, catheters used in neurovascular applications may have a braided portion in the range of thicknesses of about 0.0005 inch to about 0.003 inch.

The outer layer is then placed over the braided portion. The outer polymer layer may be in the range of from about 0.001 inch to 0.008 inch thick for catheters used in neurovascular applications. If the entire outer polymer layer has the same composition, then possible methods for adding the outer layer include: wire mandrel extrusion (in which the subassembly of coated core wire, inner polymer liner, and reinforcement act as a "wire mandrel"); dip coating or spraying using solvents and/or heat to create a solution of the material; or fuse-down techniques such as for example those employing shrink tubing. When heat is applied at selected lengths along the assembled tubular member, the outer layer material changes its form to fuse to the braided portion. The outer layer material may, for example, melt to fill or span the spaces between the braid components. Other methods known in the art than the application of heat may also be used to fuse the outer layer to the braided portion. The wire mandrel is then removed, leaving the desired composite catheter shaft tube.

It will be understood that the embodiments of the present invention which have been described are illustrative of some of the applications of the principles of the present disclosure. Numerous modifications may be made by those skilled in the art without departing from the true spirit and scope of the disclosure. Various features which are described herein can be used in any combination and are not limited to procure combinations that are specifically outlined herein.

The invention claimed is:

1. A medical catheter comprising a flexible shaft having a proximal portion and a distal end portion, said shaft having a tubular body including:
   an inner layer that defines a lumen;
   a braided portion that extends over at least a portion of said inner layer, the braided portion comprising a plurality of turn components defining a selected pic count;
   an outer layer that extends over the braided portion, the outer layer having a proximal end and a distal end;
   a fused region of the tubular body, the fused region being a first selected length of the tubular body, the first selected length including a first length of each of the inner layer, the braided portion and the outer layer, said tubular body fused region first selected length having said first length of the outer layer fused to the first length of the braided portion;
   an unfused region of the tubular body, the unfused region having a defined radius and a defined length that is a second selected length of the tubular body, the unfused region second selected length including a second length of each of the inner layer, the braided portion and the outer layer, said tubular body unfused region second selected length inner layer, braided portion and outer layer are unfused to each other and are unfused to any and all other members along the second selected length;
   said turn components of the braided portion at the fused region are fixed and non-slidable with respect to each other due to their fusion to the outer layer, while said turn components of the braided portion at the unfused region slide with respect to each other, whereby the fused region is stiffer than the unfused region, the unfused region has a greater flexibility than the fused region, and the unfused region is thereby of greater bendability than the fused region for following a vasculature path to enhance trackability;
   said fused region and said defined length unfused region being coaxial with each other; and
   wherein said outer layer at the fused region and at the unfused region have the same composition, being made of the same polymer material and being of the same durometer hardness.

2. The catheter of claim 1 wherein said outer layer is formed from a material selected from the group consisting of polyamides, polyimides, nylons, polyethylenes, PVDF, polyesterether block amides, polyurethanes and combinations thereof.

3. The catheter of claim 1 wherein said outer layer is formed from a polyesterether block amide.

4. The catheter of claim 1 wherein the material of said outer layer has a Shore durometer hardness of not greater than about 72D.

5. The catheter of claim 1 wherein the material of said outer layer has a Shore durometer hardness of from about 25D to about 60D.

6. The catheter of claim 1 wherein the material of said outer layer has a Shore durometer hardness of from about 35D to about 55D.

7. The catheter of claim 1 wherein said inner layer is formed from a material selected from the group consisting of polytetrafluoroethylene (PTFE), expanded polytetrafluoroethylene (EPTFE) and high density polyethylene (HDPE).

8. The catheter of claim 1 wherein the selected pic count of said braided portion is from about 25 to about 140 pics/inch.

9. The catheter of claim 1 wherein the selected pic count of said braided portion is from about 60 to about 120 pics/inch.

10. The catheter of claim 1 further comprising a balloon fixed to said tubular body along at least a portion of the length of the unfused region and external of the unfused region.

11. The catheter of claim 10 wherein the unfused region extends longitudinally beyond the balloon.

12. The catheter of claim 1 wherein said unfused region is at the distal end portion of said tubular body, and the remainder of said outer layer is said fused region.

13. The catheter of claim 1 wherein said outer layer is formed by extrusion of a material over the braided portion and said inner layer.

14. The catheter of claim 1 wherein said outer layer has a Shore durometer hardness of less than about 72D.

15. The catheter of claim 1 wherein said outer layer has a Shore durometer hardness of from about 25D to about 55D.

16. A balloon catheter, comprising:
   a balloon member having a proximal leg and a distal leg;
   a flexible shaft having a proximal portion and distal end portion, the shaft defining a lumen;
   a tubular body within said lumen of the flexible shaft, said tubular body including a distal end portion, an inner layer that defines a lumen, a braided portion that extends over at least a portion of said inner layer, the braided portion comprising a plurality of turn components defining a selected pic count, an outer layer that extends over the braided portion, the outer layer having a proximal and distal end;
   a fused region of the tubular body, the fused region being a first selected length of the tubular body, the first selected length including a first length of each of the inner layer, the braided portion and the outer layer, said tubular body fused region first selected length having said first length of the outer layer fused to the first length of the braided portion;
   an unfused region of the tubular body, the unfused region having a defined radius and a defined length that is a second selected length of the tubular body, the unfused region second selected length including a second length of each of the inner layer, the braided portion and the outer layer, said tubular body unfused region second selected length inner layer, braided portion and outer layer being unfused to each other and are unfused to any and all other members along the second selected length;

said turn components of the braided portion at the fused region are fixed and non-slidable with respect to each other due to their fusion to the outer layer, while said turn components of the braided portion at the unfused region slide with respect to each other, whereby the fused region is stiffer than the unfused region, the unfused region has a greater flexibility than the fused region, and the unfused region is thereby of greater bendability than the fused region for following a vasculature path to enhance trackability;

said fused region and said defined length unfused region being coaxial with each other;

said outer layer at the fused region and at the unfused region having the same composition, being composed of the same polymer material and having the same durometer hardness along its length;

said proximal leg of the balloon member is secured to said distal end portion of the flexible shaft, and said distal leg of the balloon member is secured to said distal end portion of the tubular body; and said unfused length is positioned at a location radially inward of at least a portion of said balloon between the proximal leg and the distal leg of the balloon.

17. The balloon catheter of claim 16 wherein said unfused length extends substantially the entire length of the balloon.

18. The balloon catheter of claim 16 wherein said unfused length comprises one or more unfused lengths and extends between approximately the proximal end of the proximal leg of the balloon member to the proximal end of the distal leg of the balloon member.

19. The balloon catheter of claim 16 wherein said unfused length extends proximally of the proximal end of the distal leg of the balloon member.

\* \* \* \* \*